US009174064B2

(12) United States Patent
Freeman

(10) Patent No.: US 9,174,064 B2
(45) Date of Patent: *Nov. 3, 2015

(54) SYNCHRONIZING CHEST COMPRESSION AND VENTILATION IN CARDIAC RESUSCITATION

(75) Inventor: Gary A. Freeman, Newton Center, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 298 days.

This patent is subject to a terminal disclaimer.

(21) Appl. No.: 13/116,200

(22) Filed: May 26, 2011

(65) Prior Publication Data

US 2011/0224587 A1 Sep. 15, 2011

Related U.S. Application Data

(63) Continuation of application No. 11/357,931, filed on Feb. 16, 2006, now Pat. No. 8,105,249.

(51) Int. Cl.
*A61H 31/00* (2006.01)
*A61N 1/39* (2006.01)
(Continued)

(52) U.S. Cl.
CPC ............ *A61N 1/3987* (2013.01); *A61H 31/004* (2013.01); *A61H 31/006* (2013.01);
(Continued)

(58) Field of Classification Search
CPC .............. A61H 31/004; A61H 31/006; A61H 2201/0207; A61H 2201/0214; A61H 2207/025; A61H 2201/0257; A61H 2201/0285; A61H 2201/10; A61H 2201/105; A61H 2201/107; A61H 2201/5007; A61H 2201/501; A61H 2201/5043; A61H 2201/5048; A61H 2201/5089; A61H 2230/04; A61H 2230/08; A61H 2230/205; A61H 2230/204; A61M 16/00; A61M 16/1075; A61M 2230/04; A61N 1/39; A61N 1/3987
USPC .................. 601/41–44, 108, 152, DIG. 8–10; 128/204.23, 205.19; 607/13
See application file for complete search history.

(56) References Cited

U.S. PATENT DOCUMENTS 4,198,963 A  4/1980  Barkalow et al.
4,326,507 A  4/1982  Barkalow
(Continued)

FOREIGN PATENT DOCUMENTS

DE  29909141  9/1999
FR  2382889  10/1978
(Continued)

OTHER PUBLICATIONS

European Search Report dated Apr. 5, 2012 from corresponding European Application No. 10075403.5.
(Continued)

*Primary Examiner* — Quang D Thanh
(74) *Attorney, Agent, or Firm* — Fish & Richardson P.C.

(57) ABSTRACT

Apparatus for automatic delivery of chest compressions and ventilation to a patient, the apparatus including: a chest compressing device configured to deliver compression phases during which pressure is applied to compress the chest and decompression phases during which approximately zero pressure is applied to the chest a ventilator configured to deliver positive, negative, or approximately zero pressure to the airway; control circuitry and processor, wherein the circuitry and processor are configured to cause the chest compressing device to repeatedly deliver a set containing a plurality of systolic flow cycles, each systolic flow cycle comprising a systolic decompression phase and a systolic compression phase, and at least one diastolic flow cycle interspersed between sets of systolic flow cycles, each diastolic flow cycle comprising a diastolic decompression phase and a diastolic compression phase, wherein the diastolic decompression phase is substantially longer than the systolic decompression phase.

3 Claims, 4 Drawing Sheets

(51) Int. Cl.
*A61M 16/00* (2006.01)
*A61M 16/10* (2006.01)

(52) U.S. Cl.
CPC .......... *A61M 16/00* (2013.01); *A61M 16/1075* (2013.01); *A61N 1/39* (2013.01); *A61H 2201/025* (2013.01); *A61H 2201/0207* (2013.01); *A61H 2201/0214* (2013.01); *A61H 2201/0257* (2013.01); *A61H 2201/0285* (2013.01); *A61H 2201/10* (2013.01); *A61H 2201/105* (2013.01); *A61H 2201/107* (2013.01); *A61H 2201/501* (2013.01); *A61H 2201/5007* (2013.01); *A61H 2201/5043* (2013.01); *A61H 2201/5048* (2013.01); *A61H 2201/5089* (2013.01); *A61H 2230/04* (2013.01); *A61H 2230/08* (2013.01); *A61H 2230/205* (2013.01); *A61H 2230/207* (2013.01); *A61M 2230/04* (2013.01); *Y10S 601/08* (2013.01)

(56) References Cited

U.S. PATENT DOCUMENTS

| | | | |
|---|---|---|---|
| 4,397,306 | A | 8/1983 | Weisfeldt et al. |
| 4,676,232 | A | 6/1987 | Olsson et al. |
| 5,020,516 | A | 6/1991 | Biondi et al. |
| 5,327,887 | A | 7/1994 | Nowakowski |
| 5,377,671 | A | 1/1995 | Biondi et al. |
| 5,462,524 | A | 10/1995 | Powell et al. |
| 5,490,820 | A | 2/1996 | Schock et al. |
| 5,664,563 | A | 9/1997 | Schroeder et al. |
| 5,975,081 | A | 11/1999 | Hood et al. |
| 6,171,267 | B1 | 1/2001 | Baldwin, II |
| 6,179,793 | B1 | 1/2001 | Rothman et al. |
| 6,213,960 | B1 | 4/2001 | Sherman et al. |
| 6,752,771 | B2 | 6/2004 | Rothman et al. |
| 8,105,249 | B2 * | 1/2012 | Freeman .................. 601/41 |
| 2004/0230140 | A1 | 11/2004 | Steen |
| 2005/0109339 | A1 | 5/2005 | Stahmann et al. |
| 2006/0089574 | A1 | 4/2006 | Paradis |
| 2007/0162097 | A9 | 7/2007 | Rojas |
| 2009/0107491 | A1 | 4/2009 | Belson |

FOREIGN PATENT DOCUMENTS

| | | |
|---|---|---|
| GB | 1140581 | 1/1969 |
| WO | 96/28129 | 9/1996 |

OTHER PUBLICATIONS

European Search Report dated Apr. 3, 2012 from corresponding European Application No. 10075406.8.
Crit Care Med 2000 vol. 28, No. 11 (Suppl.).
Circulation. 2005; 112:IV-58-IV-66 (Suppl.).
Circulation. Journal of the American Heart Association. 2005; 112:IV-35-IV-46.

* cited by examiner

SYNCHRONIZING CHEST COMPRESSION AND VENTILATION IN CARDIAC RESUSCITATION

CROSS-REFERENCE TO RELATED APPLICATIONS

This application is a continuation application of and claims priority to U.S. application Ser. No. 11/357,931, filed on Feb. 16, 2006, now U.S. Pat. No. 8,105,249.

TECHNICAL FIELD

This invention relates to devices for cardiac resuscitation, and more particularly to devices for automatic control of chest compression and ventilation.

BACKGROUND

Resuscitation treatments for patients suffering from cardiac arrest generally include clearing and opening the patient's airway, providing rescue breathing or ventilation with a manually operated bag-valve or powered portable ventilator apparatus for the patient, and applying chest compressions to provide blood flow to the victim's heart, brain and other vital organs. The chest compressions may be delivered by manually compressing the patient's chest in the region of the sternum or by the use of a powered chest compressor. If the patient has a shockable heart rhythm, resuscitation also may include defibrillation therapy. The term basic life support (BLS) involves all the following elements: initial assessment; airway maintenance; expired air ventilation (rescue breathing); and chest compression. When all three [airway breathing, and circulation, including chest compressions] are combined, the term cardiopulmonary resuscitation (CPR) is used.

There are many different kinds of abnormal heart rhythms, some of which can be treated by defibrillation therapy ("shockable rhythms") and some which cannot (non-shockable rhythms"). For example, most ECG rhythms that produce significant cardiac output are considered non-shockable (examples include normal sinus rhythms, certain bradycardias, and sinus tachycardias). There are also several abnormal ECG rhythms that do not result in significant cardiac output but are still considered non-shockable, since defibrillation treatment is usually ineffective under these conditions. Examples of these non-shockable rhythms include asystole, electromechanical disassociation and other pulseless electrical activity. Although a patient cannot remain alive with these non-viable, non-shockable rhythms, applying shocks will not help convert the rhythm. The primary examples of shockable rhythms, for which the caregiver should perform defibrillation, include ventricular fibrillation, ventricular tachycardia, and ventricular flutter.

After using a defibrillator to apply one or more shocks to a patient who has a shockable ECG rhythm, the patient may nevertheless remain unconscious, in a shockable or non-shockable, perfusing or non-perfusing rhythm. If a non-perfusing rhythm is present, the caregiver may then resort to performing CPR for a period of time in order to provide continuing blood flow and oxygen to the patient's heart, brain and other vital organs. If a shockable rhythm continues to exist or develops during the delivery of CPR, further defibrillation attempts may be undertaken following this period of cardiopulmonary resuscitation. As long as the patient remains unconscious and without effective circulation, the caregiver can alternate between use of the defibrillator (for analyzing the electrical rhythm and possibly applying a shock) and performing cardiopulmonary resuscitation (CPR). In the most recent version of the guidelines promulgated by the American Heart Association (AHA) in 2005, CPR may now also be delivered prior to defibrillation shocks, even for patients presenting to the rescuer with a shockable rhythm such as ventricular fibrillation. In the most recent AHA guidelines, CPR generally involves a repeating pattern of 30 chest compressions followed by a pause during which two rescue breaths are given.

Ventilation is a key component of cardiopulmonary resuscitation during treatment of cardiac arrest. Venous blood returns to the heart from the muscles and organs depleted of oxygen ($O_2$) and full of carbon dioxide ($CO_2$). Blood from various parts of the body is mixed in the heart (mixed venous blood) and pumped to the lungs. In the lungs the blood vessels break up into a net of small vessels surrounding tiny lung sacs (alveoli). The net sum of vessels surrounding the alveoli provides a large surface area for the exchange of gases by diffusion along their concentration gradients. A concentration gradient exists between the partial pressure of $CO_2$ ($PCO_2$) in the mixed venous blood ($PvCO_2$) and the alveolar $PCO_2$. The $CO_2$ diffuses into the alveoli from the mixed venous blood from the beginning of inspiration until an equilibrium is reached between the $PvCO_2$ and the alveolar $PCO_2$ at some time during the breath. When the subject exhales, the first gas that is exhaled comes from the trachea and major bronchi which do not allow gas exchange and therefore will have a gas composition similar to the inhaled gas. The gas at the end of this exhalation is considered to have come from the alveoli and reflects the equilibrium $CO_2$ concentration between the capillaries and the alveoli; the $PCO_2$ in this gas is called end-tidal $PCO_2$ ($PetCO_2$).

When the blood passes the alveoli and is pumped by the heart to the arteries it is known as the arterial $PCO_2$ ($PaCO_2$). The arterial blood has a $PCO_2$ equal to the $PCO_2$ at equilibrium between the capillaries and the alveoli. With each breath some $CO_2$ is eliminated from the lung and fresh air containing little or no $CO_2$ ($CO_2$ concentration is assumed to be 0) is inhaled and dilutes the residual alveolar $PCO_2$, establishing a new gradient for $CO_2$ to diffuse out of the mixed venous blood into the alveoli. The rate of breathing, or minute ventilation (V), usually expressed in L/min, is exactly that required to eliminate the $CO_2$ brought to the lungs and maintain an equilibrium $PCO_2$ (and $PaCO_2$) of approximately 40 mmHg (in normal humans). When one produces more $CO_2$ (e.g., as a result of fever or exercise), more $CO_2$ is produced and carried to the lungs. One then has to breathe harder (hyperventilate) to wash out the extra $CO_2$ from the alveoli, and thus maintain the same equilibrium $PaCO_2$. But if the $CO_2$ production stays normal, and one hyperventilates, then the $PaCO_2$ falls. Conversely, if $CO_2$ production stays constant and ventilation falls, arterial $PCO_2$ rises. Some portion of the inspired air volume goes to the air passages (trachea and major bronchi) and alveoli with little blood perfusing them, and thus doesn't contribute to removal of $CO_2$ during exhalation. This portion is termed "dead space" gas. That portion of V that goes to well-perfused alveoli and participates in gas exchange is called the alveolar ventilation (VA) and exhaled gas that had participated in gas exchange in the alveoli is termed "alveolar gas".

Automatic ventilators capable of delivering desired airway pressures are also known. U.S. Pat. No. 5,664,563, describes a ventilation system capable of delivering negative airway pressures. U.S. Pat. Nos. 4,676,232, 5,020,516 and 5,377,671 describe a ventilator with ventilation cycles synchronized with the cardiac cycle in order to enhance circulation. U.S. Pat. No. 4,326,507 describes a combined chest compressor and ventilator that delivers a ventilation over a number of compression cycles and then delivers another series of compression cycles during the period between ventilations.

While the current AHA recommendation is two ventilations every thirty compressions, that recommendation was promulgated in large part because it was found that the delays due to switching back and forth between compressions and ventilation by rescuers was resulting in insufficient levels of chest compressions and the resultant circulation. It is desirable, in the case of mechanical devices to integrate the functions of chest compressions and ventilations.

U.S. Pat. Nos. 6,179,793 and 6,752,771 describe an inflatable vest for assisting the heart in patients suffering from heart failure. The inflation of the vest is synchronized with on-set of the systole phase of the heart, when the left ventricular compresses to force blood out of the heart and through the aorta. The inflated vest compresses the patient's chest and increases the intrathoracic pressure. This increase in pressure assists the heart in moving blood out of the heart and through the aorta. U.S. Pat. Nos. 4,198,963 and 6,171,267 describe a device that synchronizes a chest compression cycle to the systolic phase of cardiac activity. U.S. Pat. No. 6,213,960 describes a device for automatic chest compression during resuscitation.

Synchronization of the ventilation cycle with the compression cycle is described in U.S. Pat. No. 4,397,306. The patent proposes synchronizing an automatic chest compression device with an automatic ventilator, and recommends that high pressure ventilation pulses be delivered simultaneously with the compression phase (i.e., when chest pressure is applied), and that slightly negative ventilation pulses be delivered simultaneously with the decompression phase (i.e., when no chest pressure is applied). Compression and decompression phases are of equal length (50% duty cycle). The negative ventilation pulses are said "to move greater amounts of blood into the chest during diastole". Also, the patent recommends introducing a conventional ventilation cycle every approximately sixth compression/decompression cycle, when no compression is occurring. This is said to be valuable for sufficient alveolar gas exchange since very little air flow occurs during the positive ventilation pressure cycles that are synchronized to the compression phase. While U.S. Pat. No. 4,397,306 reports that significant improvements in pressure and flow were observed using the invention, the physiological state of a typical patient differs fairly significantly from the animal model used in those experiments.

In a typical cardiac arrest, the amount of time that a patient has been without any blood flow is commonly greater than ten to twelve minutes, unlike animal models where no flow times are always less than 8 minutes, and in most experiments is less than 5 minutes. Under these prolonged conditions of ischemia, patients' vascular tone will be significantly compromised as a result of insufficient metabolic energy substrates and nitric oxide release. This loss of tone manifests itself physically with a significant increase in the compliance of the vasculature, which, like increases in capacitance in an electronic circuit, cause an increase in the intrinsic time constants of the system. This can be tested in models such as is described in Crit. Care Med 2000 Vol. 28, No. 11 (Suppl.), or in animal models with extended durations of ischemia. As the author describes, the system of differential equations has been described in a number of publications. In this specific instance, "the human circulation is represented by seven compliant chambers, connected by resistances through which blood may flow. The compliances correspond to the thoracic aorta, abdominal aorta, superior vena cava and right heart, abdominal and lower extremity veins, carotid arteries, and jugular veins. In addition, the chest compartment contains a pump representing the pulmonary vascular and left heart compliances. This pump may be configured to function either as a heart-like cardiac pump, in which applied pressure squeezes blood from the heart itself through the aortic valve, or as a global thoracic pressure pump, in which applied pressure squeezes blood from the pulmonary vascular bed, through the left heart, and into the periphery. Values for physiologic variables describing a textbook normal "70-kg man" are used to specify compliances and resistances in the model. The distribution of vascular conductances (1/resistances) into cranial, thoracic, and caudal components reflects textbook distributions of cardiac output to various body regions." In particular, the time constants of venous return during the decompression phase are significantly increased during prolonged periods of ischemia.

SUMMARY

In a first aspect, the invention features apparatus for automatic delivery of chest compressions and ventilation to a patient, the apparatus comprising a chest compressing device configured to deliver compression phases during which pressure is applied to compress the chest and decompression phases during which approximately zero pressure is applied to the chest, a ventilator configured to deliver positive, negative, or approximately zero pressure to the airway, control circuitry and processor, wherein the circuitry and processor are configured to cause the chest compressing device to repeatedly deliver a set containing a plurality of systolic flow cycles, each systolic flow cycle comprising a systolic decompression phase and a systolic compression phase, and at least one diastolic flow cycle interspersed between sets of systolic flow cycles, each diastolic flow cycle comprising a diastolic decompression phase and a diastolic compression phase, wherein the diastolic decompression phase is substantially longer than the systolic decompression phase.

Preferred implementations of this aspect of the invention may incorporate one or more of the following. The control circuitry and processor may be configured to cause the ventilator to deliver a negative ventilation pressure during the diastolic decompression phase. The time durations of the systolic compression phases and systolic decompression phases may be approximately the same. The time duration of the diastolic decompression phase may be greater than twice the time duration of the diastolic compression phase. The time duration of the diastolic decompression phase may be approximately four times the time duration of the diastolic compression phase. The diastolic flow cycle may comprise a second compression phase and a second decompression phase, and wherein the negative ventilation pressure may be delivered during one of the first and second decompression phases and a positive ventilation pressure may be delivered during the other of the first and second decompression phases. The ventilator may deliver positive and negative ventilation pressures during the systolic flow cycles. Negative ventilation pressure may be delivered during the majority of the decompression phase of the systolic flow cycle. Positive ventilation pressure may be delivered during the majority of the compression phase of the systolic flow cycle. The ventilation pressure may vary gradually in an approximately ramp shaped variation from negative to positive and back to negative, with the pressure being approximately zero at the onset of the compression phase. The pressure may change rapidly from positive to negative at or just prior to the onset of the decompression phase. The ventilation pressure waveform may be at or near a peak at the onset of decompression. The compressions and ventilations may be synchronized with the patient's ECG to augment a patient's underlying systolic and diastolic activity. The apparatus may further comprise a fluid infusion device. There may be both negative and positive pressures available from the ventilator. Oxygen levels may be elevated to greater than 40%. The apparatus may be configured to be used for victims of both cardiac and traumatic arrest wherein conditions of global ischemia may be present and the reoxygenation process during resuscitation may put the victims at risk of reperfusion injury.

In a second aspect, the invention features apparatus for automatic delivery of chest compressions and ventilation to a patient, the apparatus comprising a chest compressing device configured to deliver compression phases during which pressure is applied to compress the chest and decompression phases during which approximately zero pressure is applied to the chest, a ventilator configured to deliver positive, negative, or approximately zero pressure to the airway, control circuitry and processor, wherein the circuitry and processor are configured to cause the chest compressing device to repeatedly deliver systolic flow cycles, each systolic flow cycle comprising a systolic decompression phase and a systolic compression phase, and wherein the control circuitry and processor are configured to cause the ventilator to deliver a ventilation pressure during the compression phase that increases from approximately zero pressure at the onset of the compression phase to approximately a maximum at or near the end of the compression phase.

Preferred implementations of this aspect of the invention may incorporate one or more of the following. The control circuitry and processor may be configured to cause the ventilator to deliver a ventilation pressure that is negative at the onset of the decompression phase. Fluids infused by the infuser may be configured to provide metabolic substances during reperfusion. The substances may be amino acids. The amino acids may be aspartate or glutamate. The apparatus may further comprise a defibrillator and infuser, and wherein the defibrillator, compressor, ventilator, and infuser may be separate devices and may be linked by a communications link. The apparatus may also further comprise an additional device to synchronize the defibrillator, compressor, ventilator, and infuser.

In a third aspect, the invention features apparatus for automatic delivery of chest compressions and ventilation to a patient, the apparatus comprising a chest compressing device configured to deliver compression phases during which pressure is applied to compress the chest and decompression phases during which approximately zero pressure is applied to the chest, a ventilator configured to deliver positive, negative, or approximately zero pressure to the airway, cooling apparatus for cooling gases delivered by the ventilator, wherein the cooling is configured to cool the lungs, heart and the pulmonary blood flow.

Among the many advantages of the invention (some of which may be achieved only in some of its various aspects and implementations) are the following. Improved blood flow is achieved by alternating a set of systolic flow cycles with at least one diastolic flow cycle. The diastolic flow cycle has a lengthened decompression phase synchronized with a negative ventilation pressure The lengthened diastolic flow cycle provides more time for venous filling, and thus better blood flow than could be achieved with the approach taught in U.S. Pat. No. 4,397,306.

Other features and advantages of the invention will be found in the detailed description, drawings, and claims.

DETAILED DESCRIPTION

There are a great many possible implementations of the invention, too many to describe herein. Some possible implementations that are presently preferred are described below. It cannot be emphasized too strongly, however, that these are descriptions of implementations of the invention, and not descriptions of the invention, which is not limited to the detailed implementations described in this section but is described in broader terms in the claims.

Figure 1:
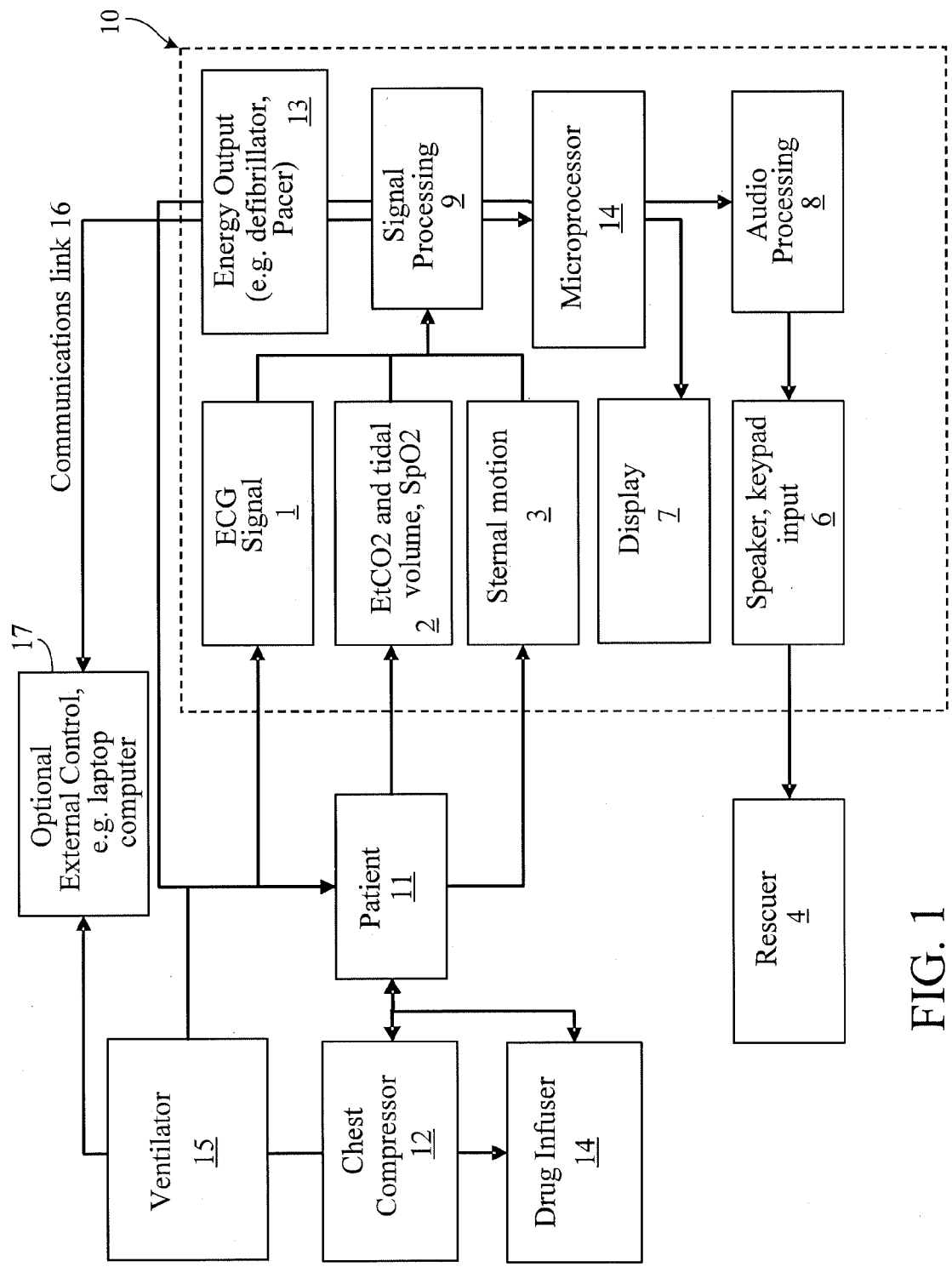
FIG. 1 is a block diagram of one implementation of the invention.

FIG. 1 shows a block diagram of one implementation. Microprocessor 14 controls in an integrated fashion the ventilator functions 15, chest compressor 12, drug infuser 14, and defibrillator/pacer 13. Physiological sensors 2, sternal motion measurement methods such as accelerometer-based sternal displacement measurement 3, and signal processing 9 to filter and process these various signals such as end-tidal carbon dioxide measurement ($EtCO_2$) and pulse oximetry ($SpO_2$) are used to determine the patient's 11 physiological and physical state. A separate laptop 17 may communicate with the microprocessor 14, and may, in fact, be used to control the therapy delivered by the ventilator 15, chest compressor 12, drug infusor 14, and defibrillator 13.

Figure 2:
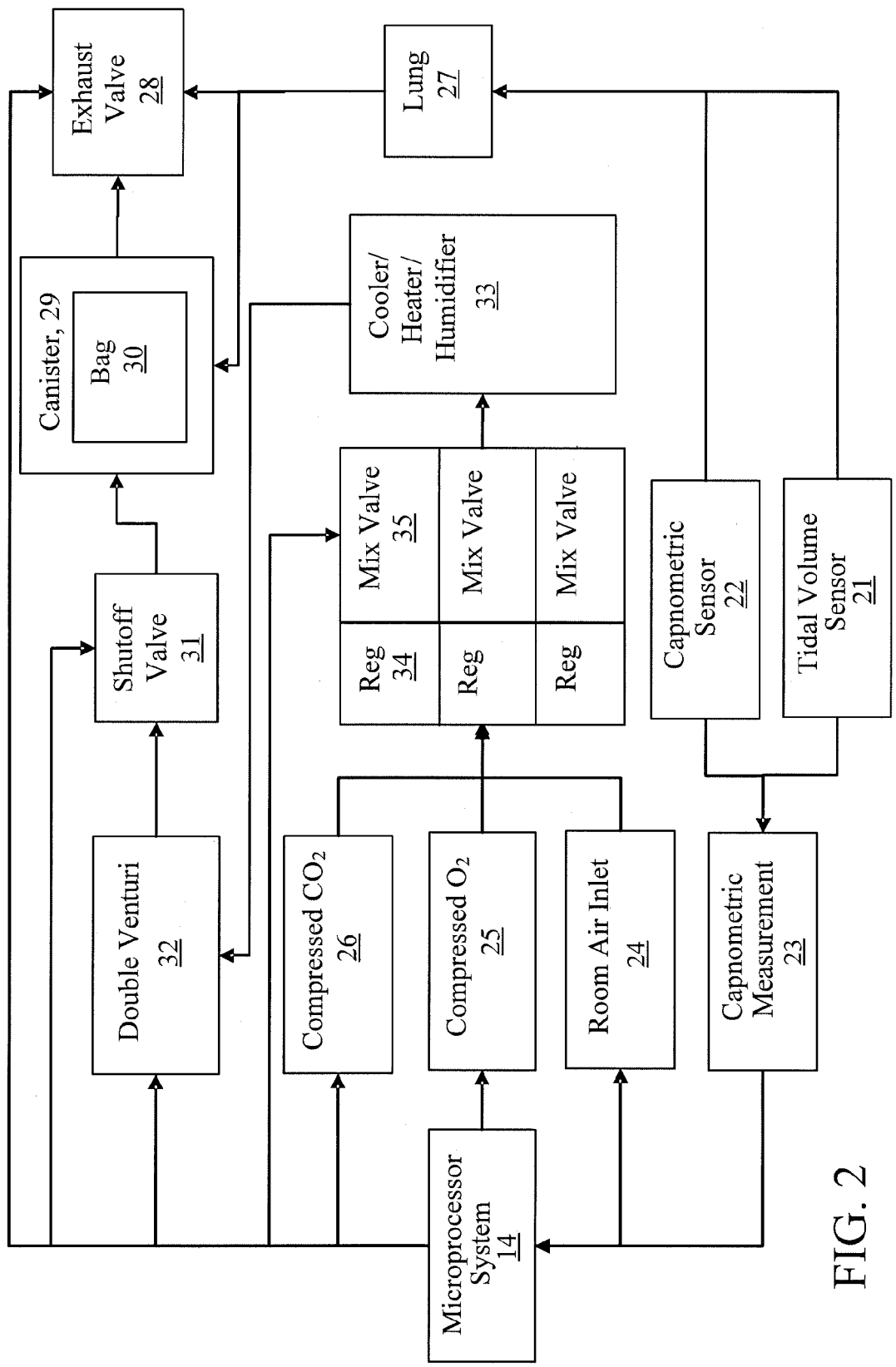
FIG. 2 is a block diagram of the ventilator of one implementation of the invention.

Referring to FIG. 2, which shows a block diagram of the ventilator portion of one implementation, microprocessor 14 controls the delivery of various therapeutic gases, compressed $CO_2$ 26, $O_2$ 25, and room air 24. Pressures for these gases are controlled by regulators 34 and mixed with valves 35 to achieved the desired partial pressures for each of the gases. A cooler/heater/humidifier 33 is provided to condition the air. In one implementation, a heat exchanger is provided that cools the gas mixture to 1-2 degrees centigrade as a means of inducing mild hypothermia. The heat exchanger may be an electrically-powered element incorporating a Peltier-effect element or may incorporate a cold storage element such as a liquid nitrogen or dry ice storage element. In the case of the cold storage element, the rate of cooling is controlled by insulating the cold storage element, providing for a heat conducting window in the insulation, and adjusting the surface area of the heat conducting window.

Figure 3:
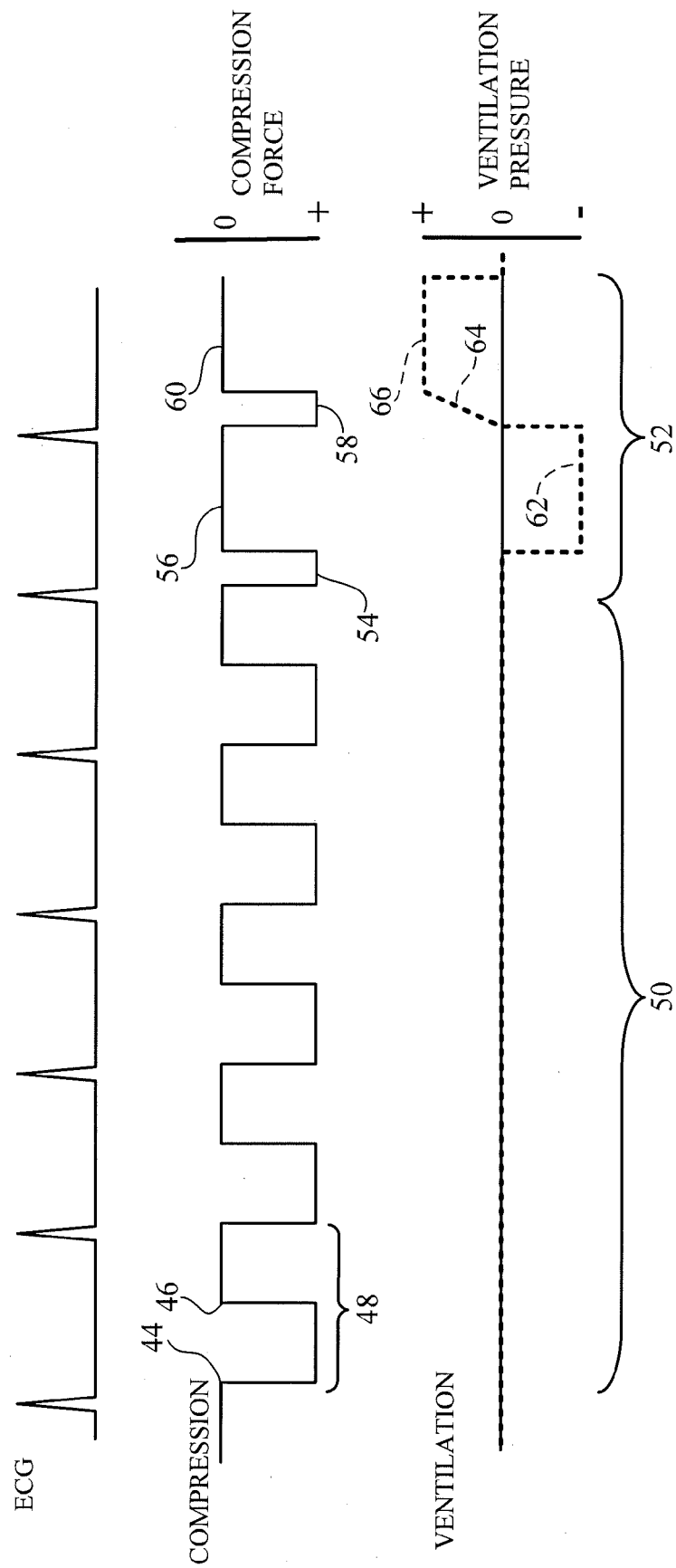
FIG. 3 is a timing diagram of the integrated compression and ventilation cycles of one implementation of the invention.

FIG. 3 shows a timing diagram of one implementation. Three waveforms are shown. First is the patient's ECG (the ECG shown is representative of an ECG following return of spontaneous circulation (ROSC); a very different ECG would typically be present prior to ROSC). The second waveform is the chest compression force applied by the automatic chest compression device (in the figure, compression pressure rises as the waveform moves downwardly). The third waveform is the ventilation pressure applied to the airway (in the figure, pressure is positive above the axis, and negative below the axis).

In some implementations, the compression-to-ventilation ratios can be varied from the current AHA recommendation of two ventilations every 30 seconds. For example, one ventilation may be delivered for every five chest compressions (a ratio closer to that of a normal adult).

In the implementation shown in FIG. 3, there are five chest compression cycles 48 during period 50. Each compression cycle has a 50% duty cycle of compression to decompression ratio and an 800 msec cycle length (400 msec compression phase; 400 msec decompression phase). Each cycle includes an onset of compression or downstroke (44) and an onset of decompression or upstroke (46). These compression cycles are configured to improve systolic flow, and so can be called "systolic flow cycles".

Following the five systolic flow cycles, there is a "diastolic flow cycle" 52. The diastolic flow cycle begins with a shortened compression phase 54 of 200 msec duration, followed by a lengthened decompression phase 56 of 600 msec duration, then a second shortened compression phase 58 (200 msec), and a second lengthened decompression phase 60 (600 msec). During the diastolic flow cycle, the automatic ventilator produces a negative pressure phase 62 (600 msec) to induce a negative intrathoracic pressure (approx. −2 kPa) aligned with decompression phase 56. This results in increased venous return to the right atrium (diastolic flow), thus increasing blood flow during the subsequent compression phase 58. The ventilation pressure ramps up (64) to approximately +2 kPa during the compression phase 58 and remains constant at +2 kPa during the subsequent 600 msec decompression phase 66. In the implementation of FIG. 3, ventilation assistance is not provided during the systolic flow cycles (ventilation pressure is zero during those cycles).

Figure 4:
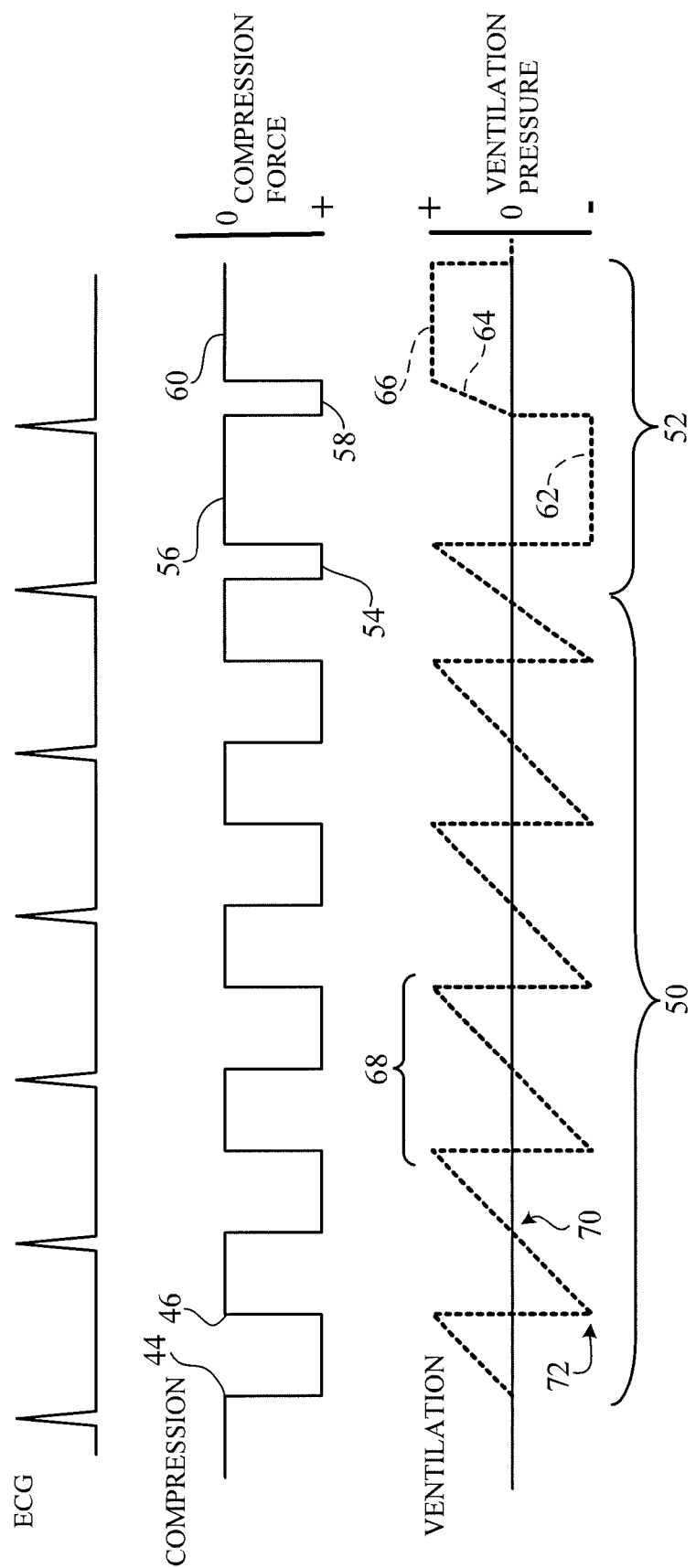
FIG. 4 is a timing diagram of the integrated compression and ventilation cycles of another implementation of the invention.

FIG. 4 shows another implementation, in which systolic flow may be further enhanced by short ventilation cycles 68 synchronized with the systolic flow cycles 50. The ventilation cycles are synchronized with the compression and decompression phases of the systolic flow cycles, taking the shape of a ramp with approximately zero pressure at the onset 70 of the compression phase, and rising to a maximum positive pressure during the compression phase. In the decompression phase of the cycle, a similar triangular ventilation pressure waveform is used, with the maximum negative pressure 72 occurring just slightly prior to (approximately 40 msec prior) to the onset of the decompression phase, so that the airway pressure is definitively negative at the onset of decompression, so as to maximize diastolic reflow. This linear ramp with a zero-crossing at the onset of compression has the advantage of providing an airway that is close to a homogeneously neutral pressure at the onset of compression, so that at the compression downstroke 44 and the resultant rise in intrathoracic pressure, the airway collapses for a portion of the compression phase. By collapsing the airway, the volume of the lungs themselves are maintained during the chest compression cycle, acting effectively as bellows on each side of the heart to squeeze the heart during a compression thus enhancing systolic flow. In some implementations, chest compression is provided by a load-distributing band such as that manufactured by ZOLL Circulatory Systems of Sunnyvale Calif. The diastolic flow cycles 52 occur after a number, preferably five or six, of systolic flow cycles 50. The diastolic flow cycle may have approximately a 20-30% compression duty cycle, with a decompression phase 62 that is approximately 640 msec in duration. Subsequent to ROSC, a victim's own heart is pumping and circulating blood, but usually with reduced efficiency. In some implementations, ventilations after ROSC are delivered without compressions. But in other implementations, compressions after ROSC may also be delivered in a similar pattern to that used during cardiac arrest. The compressions after ROSC differ in two important respects: (1) they are synchronized to the QRS of the patient's ECG, as shown in FIG. 3; and (2) they are of reduced compressive force. A compression of reduced force and synchronized to the ECG QRS will augment the natural flow of the patient's hemodynamics enhancing recovery.

Many other implementations other than those described above are within the invention, which is defined by the following claims. For example, different shapes and different numbers of compression and ventilation waveforms than those shown in FIGS. 3 and 4 may be used.

What is claimed is:

1. Apparatus for automatic delivery of chest compressions and ventilation to a patient, the apparatus comprising:
   a chest compressing device configured to deliver compression phases during which pressure is applied to compress the chest and decompression phases during which approximately zero pressure is applied to the chest;
   a ventilator configured to deliver positive, negative, or approximately zero pressure to the airway;
   control circuitry and processor, wherein the circuitry and processor are configured to cause the chest compressing device to repeatedly deliver systolic flow cycles, each systolic flow cycle comprising a systolic decompression phase and a systolic compression phase and being configured to improve systolic circulatory flow, and
   wherein the control circuitry and processor are configured to cause the ventilator to deliver a ventilation pressure during the systolic compression phase that increases in the shape of a ramp over the duration of the systolic compression phase from approximately zero pressure at the onset of the systolic compression phase to approximately a maximum pressure at or near the end of the compression phase, and transitions to a negative minimum pressure at or near the start of the decompression phase, and then increases in the shape of a ramp over the duration of the systolic decompression phase to approximately zero pressure at the end of the decompression phase.

2. The apparatus of claim 1 further comprising cooling apparatus for cooling gases delivered by the ventilator, wherein the cooling is configured to cool the lungs, heart and the pulmonary blood flow.

3. The apparatus of claim 1 wherein the slope of the ramp shape during the decompression phase is approximately the same as the slope during the compression phase.

* * * * *